United States Patent [19]

Edelman et al.

[11] Patent Number: 4,657,014

[45] Date of Patent: Apr. 14, 1987

[54] LIQUID INTERFACE FIBEROPTIC COUPLER

[75] Inventors: William Edelman, Seal Beach; Hamid R. Naghieh, Santa Ana; Dennis Constantinou, Irvine, all of Calif.

[73] Assignee: Shiley, Inc., Irvine, Calif.

[21] Appl. No.: 710,184

[22] Filed: Mar. 11, 1985

[51] Int. Cl.⁴ .............................................. A61B 17/36
[52] U.S. Cl. .................... 128/303.1; 350/96.15
[58] Field of Search ........................... 128/4–8, 128/303.1, 395–398, 633, 634; 219/121 LA, 121 LP; 350/1.5, 96.65, 96.23, 267, 418

[56] References Cited

U.S. PATENT DOCUMENTS

| | | |
|---|---|---|
| 3,467,098 | 9/1969 | Ayres . |
| 3,471,215 | 10/1969 | Snitzer . |
| 4,207,874 | 6/1980 | Choy . |
| 4,341,205 | 7/1982 | Hosono et al. ............... 128/4 |
| 4,350,163 | 9/1982 | Ford et al. .................. 128/633 |
| 4,408,602 | 10/1983 | Nakajima ............... 128/303.1 |
| 4,418,688 | 12/1983 | Loeb . |
| 4,421,382 | 12/1983 | doi et al. ............... 128/303.1 |
| 4,423,736 | 1/1984 | De Witt et al. .......... 128/633 |
| 4,448,188 | 5/1984 | Loeb . |
| 4,449,535 | 5/1984 | Renault ................... 128/634 |
| 4,470,407 | 9/1984 | Hussein ................... 128/398 |
| 4,473,074 | 9/1984 | Vassiliadis .............. 128/303.1 |

OTHER PUBLICATIONS

Denise Grady, "The Artery Zapper" Dec. 1982, Discovery p. 36.

*Primary Examiner*—Edward M. Coven
*Assistant Examiner*—Max F. Hindenburg
*Attorney, Agent, or Firm*—Charles J. Knuth; Peter C. Richardson; Mark Dryer

[57] ABSTRACT

A device for conveying high energy electromagnetic radiation from a laser source to an optical fiber which comprises a sleeve having a proximal end and a distal end and being adapted to enclose a liquid which is transparent to said radiation, the distal end of said sleeve being adapted to be attached to the input end of the optical fiber; and a focussing lens attached to the proximal end of said sleeve said liquid having a refractive index which substantially matches the refractive index of the lens and of the optical fiber. A process for removing an obstruction by laser surgery using said device is also disclosed.

6 Claims, 4 Drawing Figures

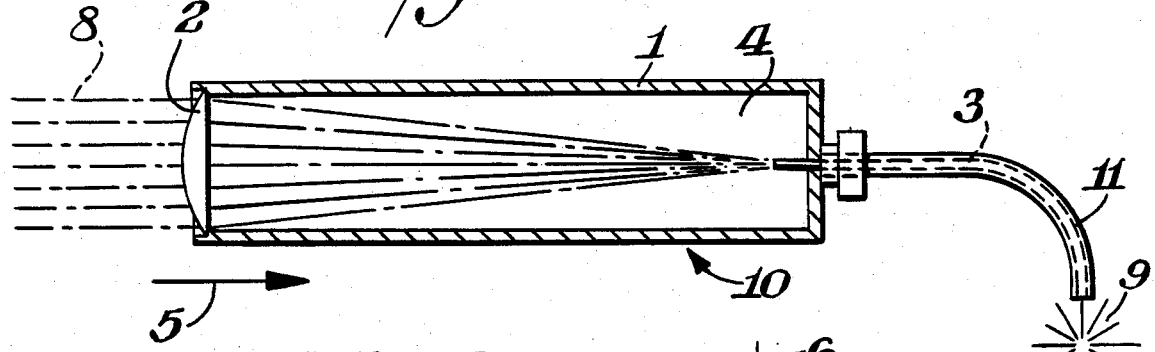
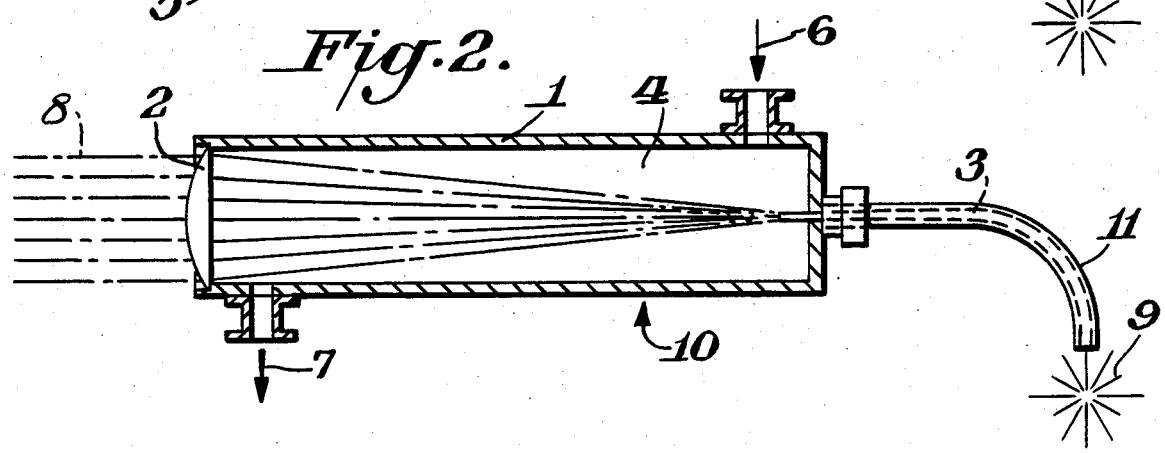
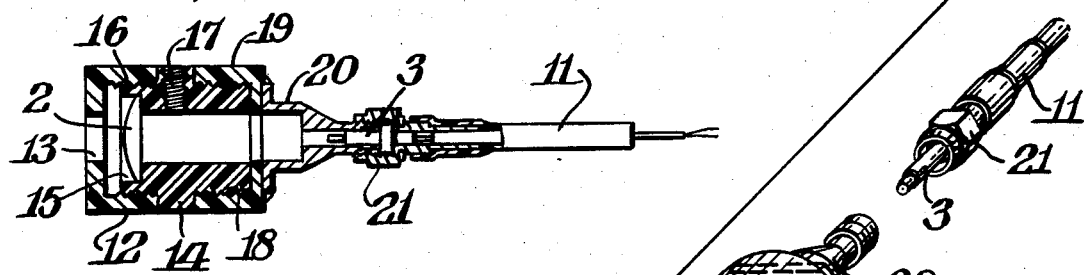
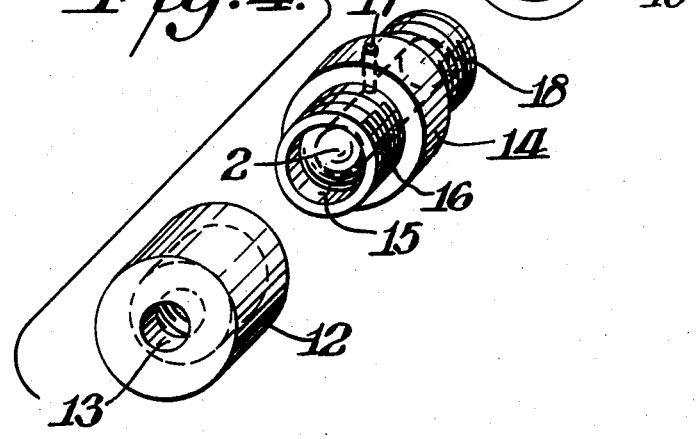

LIQUID INTERFACE FIBEROPTIC COUPLER

BACKGROUND OF THE INVENTION

This invention relates to a device for conveying high energy electromagnetic radiation from a laser source through an optical fiber to a target, said device being in the form of a liquid interface fiberoptic coupler.

The device of the invention is particularly adapted to be used in apparatus for directing laser radiation on to targets such as vascular obstructions and atherosclerotic lesions.

The common disease atherosclerosis, which is a type of arteriosclerosis, is characterized by the formation of atherosclerotic lesions (also known as atherosclerotic plaques) on the inner wall of the aorta and the large and medium-sized arteries. The most important symptom in the early stages of this disease is hypertension. If uncorrected, however, the disease can lead to total blood vessel blockage, and ultimately, death of the patient. The atherosclerotic lesions are masses of fatty material associated with fibrous connective tissue, very often with secondary deposits of calcium salts and blood constituents. Human atherosclerotic lesions are characterized by a large lipid content, which may account for as much as 60 percent of the dry weight of some advanced lesions. Three major classes of lipids are found, i.e. cholesterol, cholesterol esters and phospholipids.

One technique currently practiced for correcting problems arising from arteriosclerotic lesions is coronary or peripheral arterial bypass surgery, in which a blood vessel segment removed from another part of the patient's body, e.g. a saphenous vein segment, or a synthetic vascular graft is implanted in parallel with the occluded artery. Although arterial bypass surgery has been practiced with great success for many years, it is a major surgical operation with inevitable attendant risks and the medical profession therefore has continued to search for techniques for reducing vascular obstructions such as arteriosclerotic lesions without bypass surgery.

Another technique currently practiced with considerable success in the treatment of arteriosclerosis is transluminal angioplasty, in which a balloon catheter is inserted into an affected blood vessel and the balloon then expanded outwardly against the occlusion to recannulate the vessel. One disadvantage of this technique is that it cannot be employed when the vessel is already fully blocked (or almost so) by occlusions. Also, it results principally in redistribution (i.e. compaction) rather than physical or chemical removal of the lesion material, most of which remains in the affected blood vessel wall and can serve as a site for future occlusive growth.

Recently it has been proposed to reduce vascular occlusions such as arteriosclerotic lesions by laser revascularization, in which electromagnetic radiation generated by a laser is carried by one or more optical fibers to the vicinity of the occlusion and directed at the occlusion. Uptake of the laser radiation by occlusion material results in its conversion to relatively low molecular weight organic substances, which are dissolved in and carried away by the blood stream. Examples of apparatus for the practice of laser revascularization are disclosed in U.S. Pat. No. 4,207,874; U.S. Pat. No. 4,418,688; World Published Patent Application 8301893, published June 9, 1983; World Published Patent Application No. 8303188, published Sept. 29, 1983 and World Published Patent Application No. 8302885, published Sept. 1, 1983. A significant advantage of laser revascularization is that it can result in the essentially complete removal of a vascular occlusion (e.g. an arteriosclerotic lesion) in a surgical procedure that is far less invasive than bypass surgery. However, because of the difficulty in designing a laser catheter system whose use assures that the laser beam is carefully directed to impinge only upon the undesired occlusion, the practice of this technique involves a risk of damage to blood constituents and healthy surrounding tissues, particularly the surrounding non-arteriosclerotic blood vessel tissue.

Commonly assigned Patent Application Ser. No. 573,448 discloses a method for the reduction of an arteriosclerotic lesion without significant risk of damage to surrounding blood and healthy tissues involving the use of electromagnetic radiation in which substantially all of the electromagnetic radiation directed at the lesion is of a wavelength in the ultraviolet or visible region at which energy is selectively absorbed, as compared to absorption by whole blood and non-arteriosclerotic blood vessel tissue, by a lesion component present in said lesion at a greater weight percentage (on a dry basis) than in the whole blood or surrounding non-arteriosclerotic blood vessel tissue of the patient. The ensuing reaction and decomposition of said lesion component leads directly to the reduction of the lesion without significant risk of damage to the vicinal blood or, should the electromagnetic radiation be inadvertently misdirected, to the surrounding healthy tissues. The electromagnetic radiation directed at the lesion is preferably monochromatic, i.e. substantially all within an extremely narrow wavelength range. Preferably, monochromatic electromagnetic radiation is generated by a laser and conducted to the vicinity of the lesion by at least one optical fiber. Monochromatic ultraviolet energy is preferably generated by an excimer laser.

Thus, cholesterol, which is a common component of arteriosclerotic lesions, selectively absorbs electromagnetic radiation having a wavelength of about 248 nanometers and treatment as described above with laser radiation of said wavelength leads to reduction of the lesion.

As used herein, the term "reducing an arteriosclerotic lesion", or the like, means substantially reducing the size of the lesion. Preferably, treatment is continued until essentially complete removal of the lesion has been achieved.

The use of electromagnetic radiation of a particular wavelength to selectively reduce or obliterate arteriosclerotic lesions does not depend upon the use of a particular delivery system but only upon the use of the type of radiation. However, without the use of a coupler system as described herein the efficiency of the energy transfer from the laser to the optical fiber is greatly reduced.

It has now been found that the operation of a system using a laser source of electromagnetic radiation and directing said radiation to a target through one or more optical fibers is significantly improved and degradation of the optical fiber is reduced if the radiation from the laser to the optical fiber is conveyed through a coupling device, more particularly a liquid coupler.

SUMMARY OF THE INVENTION

In accordance with the present invention there is provided a device for conveying high energy electromagnetic radiation from a laser source to an optical fiber which comprises a sleeve having a proximal end and a distal end and being adapted to enclose a liquid which is transparent to said radiation, the distal end of said sleeve being adapted to be attached to the input end of the optical fiber; and a focussing lens attached to the proximal end of said sleeve, said liquid having a refractive index which substantially matches the refractive index of the lens and of the optical fiber.

The device of the invention, although not restricted thereto, is particularly adapted for use in laser revascularization and, accordingly, the invention also provides a process for removing an obstruction by laser surgery which comprises subjecting the said obstruction to high energy electromagnetic radiation conveyed through an optical fiber which is coupled to a laser by a liquid which is transparent to said radiation and is enclosed in a sleeve having a proximal end and a distal end and which sleeve is attached at its distal end to the input end of the optical fiber and at its proximal end to a focussing lens associated with the aperture of the laser, wherein the liquid has a refractive index which substantially matches the refractive index of the lens and of the optical fiber.

It is to be understood that although the preferred application of the device of the invention is in the art of laser surgery, and the invention will be particularly described herein with reference to such application, the device is also useful in any application where coupling between a laser source and a radiation applicator is necessary or desirable to concentrate or focus the electromagnetic radiation and/or to protect or preserve the applicator, e.g. optical fiber. A typical example of an alternative utility is in the art of high energy laser welding.

DETAILED DESCRIPTION OF THE INVENTION

The device according to the invention which is essentially a liquid interface fiberoptic coupler, allows the transfer of high energy content electromagnetic radiation, particularly ultraviolet (UV) radiation, from a laser into an optical fiber. Preferably the coupler device is adapted to operate with a laser producing radiation having a wavelength of from 100 to 2000 nm, more preferably about 248 nm.

In a particularly preferred embodiment the laser is a krypton fluoride excimer laser producing UV radiation having a wavelength of 248 nm with a low absorption through water.

The coupler device of the invention not only preserves the energy content of the laser impulse but also allows for the preservation of the fiber input surface. Since it is almost impossible to polish the surface of an optical fiber to eliminate imperfections having a thickness less than one laser wavelength, which in the case of said excimer laser is 0.2 micron, the liquid coupling device acts as a physical extension of the fiber wherein the liquid fills the imperfections on the fiber surface and thus allows energy transfer through the liquid medium and into the input surface of the fiber without damaging the fiber surface. This is achieved by index matching of the fiber material and the liquid medium.

In a preferred embodiment the liquid medium is distilled water which has a refractive index of about 1.33 at a wavelength of 248 nm (2.48 microns). The index of refraction of fused silica, which is the preferred material for the optical fiber, is about 1.43 at the said wavelength of 248 nm.

Other liquid media which are suitable for use in the device of the invention are an aqueous solution of 3.74 M potassium chloride having a refractive index of about 1.37 at the said wavelength of 248 nm; and a 3% hydrogen peroxide solution having a refractive index of about 1.33 at the said wavelength.

In the operation of the device according to the invention electromagnetic radiation, for example UV radiation having a wavelength of 248 nm, from a laser enters the coupler through an aperture which removes any aberration present in the initial laser beam. The radiation then passes through a focussing lens which, preferably, is a single element lens made from the same material as the optical fiber, for example, fused silica. The focussed beam from the lens then passes through the liquid medium and then into the input surface of the optical fiber.

If desired, the coupler may be inserted in a coupler holder. Thus, a metal sleeve may be used to align the coupler over its length with respect to the laser beam, so that the beam enters the coupler normal to the lens surface.

DESCRIPTION OF THE DRAWINGS

The invention will be more particularly described with reference to preferred embodiments as illustrated in the accompanying drawings, in which:- FIG. 1 is a schematic representation of one embodiment of the invention;

FIG. 2 is a schematic representation of another embodiment of the invention;

FIG. 3 is an axial cross-sectional view of an actual device according to the invention; and FIG. 4 is a perspective view, in exploded form, of the component parts of the device illustrated in FIG. 3, excluding the focussing lens.

The device illustrated schematically in FIG. 1 is a coupler 10 comprising a cylindrical sleeve 1 having a lens 2 attached, in a recess, at the proximal end and an optical fiber 3 attached at the distal end.

The sleeve may be made from a metal, such as stainless steel or aluminum, or from a plastics material, such as ABS, Delrin or Lexan. The sleeve is filled with a liquid 4 having a refractive index which substantially matches the refractive index of the lens and of the optical fiber.

The liquid may be a static homogeneous liquid of constant refractive index throughout, for example distilled water, or, in an alternative embodiment, the liquid may be a solvent/solute system of increasing concentration as indicated by the arrow 5. It is to be understood that the concept of a concentration gradient is not inconsistent with the requirement that the refractive index of the liquid should substantially match that of the optical fiber. The small variation in the refractive index of the solution resulting from the concentration gradient provides a supplementary focussing mechanism which enhances the primary focussing by lens 2. The focussing mechanism bends the electromagnetic radiation passing through the liquid toward the input surface of the optical fiber without concentrating the energy to a point at which it would cause material breakdown in the optical fiber.

In an alternative embodiment as illustrated in FIG. 2 the liquid flows through the device, entering the sleeve at inlet 6 and leaving at outlet 7. The significance of the liquid flow system is to eliminate possible contaminants which may result from scattered radiation against the wall of the sleeve. It has been found that the liquid may degrade over a period of time in the presence of certain sleeve material contaminants, such as stainless steel, and these contaminants are eliminated by the flowing liquid arrangement.

In a preferred embodiment of the liquid flow system the sleeve is made from a clear transparent polymer, for example a thermoplastic carbonate-linked polymer produced by reacting bisphenol A and phosgene and available commercially under the trademark "Lexan". In such an embodiment the lens, made of fused silica, is retained by inner annular rings of polyvinyl chloride (PVC) held in place through a water-tight pressure fit by O-ring washers. The optical fiber, also made of fused silica, is attached to another annular ring of PVC at the distal end of the sleeve. The flow of liquid through this embodiment is carefully controlled so that the desired refractive index is obtained.

Electromagnetic radiation from an excimer laser enters the sleeve through an aperture as a substantially parallel beam 8. The beam is focussed through the lens 2 into a cone-shaped beam which enters the input end of the optical fiber 3 through which it is conveyed, as a concentrated beam of energy, to the desired target 9. The optical fiber is preferably protected over a substantial portion of its length by a sheath 11 of black flexible PVC. Although the sheath is not essential for the operation of the fiber, it is a desirable feature since it allows for increased bend radius in the fiber material, e.g. fused silica, and protects the cladding of the fiber from damage during use.

The optical fiber is attached to the distal end of the sleeve either through a standard optical fiber screw thread (see FIGS. 3 and 4) or through solvent bonding or heat bonding of the fiber directly to the end of the sleeve.

An actual device in accordance with the static liquid embodiment illustrated schematically in FIG. 1 is shown in more detail in FIGS. 3 and 4.

The sleeve of the device illustrated in FIG. 3 is a three-element cylindrical body with an axial bore. Each of the elements is made of a black polymeric material which is an acetal resin commercially available under the trademark "Delrin". The proximal element 12 has an aperture 13 through which electromagnetic radiation from a laser (not shown) enters the device and is focussed by the lens 2. The central element 14 has a recess 15 in which the focussing lens is located and is secured in a water-tight position by screwing the proximal threaded male portion 16 of the central element into the female thread of the proximal element. The desired watertight fit may be ensured by the use of an appropriate rubber or plastic gasket (not shown).

A suitable liquid, preferably distilled water, is introduced into the central bore of the device through inlet hole 17 and the hole is closed with an appropriate screw or bung (not shown).

The distal threaded male portion 18 of the central element screws into the female threaded portion of the distal element 19 forming a water-tight fit therewith. If desired an appropriate gasket or washer (not shown) may be used to ensure a water-tight fit.

A metal connector 20 having a central bore and a male screw thread at its distal end is bonded or riveted to the distal end of element 19. The female threaded portion 21 of the connector is bonded to the inlet end of the optical fiber 3 and when the connector is screwed together the optical fiber is securely attached, in a water-tight fit, to the distal end of the device.

FIG. 4 illustrates the relationship between the various components of the device, other than the lens, as described above with reference to FIG. 3.

Typical dimensions for a preferred embodiment of the invention as illustrated in FIG. 3 and 4 are as follows:

Core diameter of the optical fiber is from 200 to 1000 microns, preferably 200 to 600 microns.

The optical fiber material is fused silica having a refractive index of about 1.43.

The length of the fiber is from 0.5 to 2.5 meters, preferably about 2 meters.

The above embodiment is adapted to operate with laser electromagnetic radiation having a wavelength from 100 nm to 400 nm. Particularly preferred is UV radiation having a wavelength of 248 nm from a krypton fluoride excimer laser.

The embodiment of the invention described above is particularly adapted for use in laser surgery. For such operation the optical fiber may be inserted directly into an artery or, alternatively, in order to observe the effect of the laser radiation on an atherosclerotic lesion, it is advantageous to open the artery longitudinally and to position the fiber perpendicularly over the target in order to photograph the laser action as it obliterates the atherosclerotic plaque. This type of procedure normally would be performed by a vascular surgeon or cardiovascular surgeon.

The fiber is also adapted to be inserted percutaneously into an artery for obliterating subtotal or occlusive atherosclerotic lesions.

We claim:

1. A coupling device for conveying high energy electromagnetic radiation from an excimer laser source to an optical fiber to reduce degradation of the fiber, which comprises a sleeve means having a proximal end and a distal end for enclosing a liquid which is transparent to said radiation, the distal end of said sleeve means having attachment means for attaching said distal end to the input end of the optical fiber; and a focussing lens attached to the proximal end of said sleeve means, said liquid having a refractive index which substantially matches the refractive index of the lens and of the optical fiber to enhance the energy transfer from the laser to the optical fiber and thereby reduce degradation of the fiber.

2. A device according to claim 1, in which the liquid is distilled water having a refractive index of 1.33 at said wavelength and the optical fiber is fused silica having a refractive index of 1.43 at said wavelength.

3. A device according to claim 1, in which the sleeve is cylindrical and is made from a metal or a plastics material.

4. A device according to claim 1, in which the lens is a single element lens made from the same material as the optical fiber.

5. A device according to claim 1, which the liquid is an aqueous solution of 3.74M potassium chloride having a refractive index of 1.37 at the said wavelength.

6. A device according to claim 1, in which the liquid is a 3% hydrogen peroxide solution having a refractive index of 1.33 at the said wavelength.

* * * * *